(12) United States Patent
Wang et al.

(10) Patent No.: US 8,816,084 B1
(45) Date of Patent: Aug. 26, 2014

(54) CRYSTALS OF MORPHINAN DERIVATIVE, MANUFACTURING METHOD THEREOF, AND PHARMACEUTICAL COMPOSITION USING THE SAME

(71) Applicant: Everlight Chemical Industrial Corporation, Taipei (TW)

(72) Inventors: Yuan-Yi Wang, Taoyuan County (TW); Yu-Kai Li, Taoyuan County (TW); Yu-Ting Su, Taoyuan County (TW); Chia-Chen Hung, Taoyuan County (TW); Chi-Hsiang Yao, Taoyuan County (TW)

(73) Assignee: Everlight Chemical Industrial Corporation, Taipei (TW)

( * ) Notice: Subject to any disclaimer, the term of this patent is extended or adjusted under 35 U.S.C. 154(b) by 0 days.

(21) Appl. No.: 14/165,813

(22) Filed: Jan. 28, 2014

(30) Foreign Application Priority Data

Apr. 26, 2013 (TW) .............................. 102115012 A (51) Int. Cl.
*C07D 489/00* (2006.01)
*C07D 489/08* (2006.01)

(52) U.S. Cl.
CPC .................................... *C07D 489/08* (2013.01)
USPC .................................. 546/44; 546/45; 546/46

(58) Field of Classification Search
None
See application file for complete search history.

(56) References Cited

U.S. PATENT DOCUMENTS 7,803,942 B2 * 9/2010 Wakita et al. ................... 546/44

* cited by examiner

*Primary Examiner* — Janet L Andres
*Assistant Examiner* — Timothy R Rozof
(74) *Attorney, Agent, or Firm* — Bacon & Thomas, PLLC (57) ABSTRACT

The present invention relates to a X-form crystal of 17-cyclopropylmethyl-3,14β-dihydroxy-4,5α-epoxy-6β-[N-methyl-trans-3-(3-furyl)acrylamido]morphinan hydrochloride and the manufacturing method thereof, wherein the X-form crystal of the compound has characteristic diffraction peaks at positions of 2θ of 13.6°(±0.2°), 17.2°(±0.2°), 19.1°(±0.2°), 23.2°(±0.2°), and 23.8°(±0.2°) in a powder X-ray diffraction pattern thereof. The present invention also relates to a pharmaceutical composition comprising the above-mentioned X-form crystal of morphinan derivative hydrochloride.

10 Claims, 4 Drawing Sheets

CRYSTALS OF MORPHINAN DERIVATIVE, MANUFACTURING METHOD THEREOF, AND PHARMACEUTICAL COMPOSITION USING THE SAME

CROSS REFERENCE TO RELATED APPLICATION

This application claims the benefits of the Taiwan Patent Application Serial Number 102115012, filed on Apr. 26, 2013, the subject matter of which is incorporated herein by reference.

BACKGROUND OF THE INVENTION

1. Field of the Invention

The present invention relates to a crystal of morphinan derivative, a manufacturing method thereof, and a pharmaceutical composition using the same, and more particularly to a crystal of morphinan derivative prepared using a hydrogen chloride organic solution, a manufacturing method thereof, and a pharmaceutical composition using the same.

2. Description of Related Art

In general, in the medical field, compounds of different crystal forms may have different physical properties such as solubility, dissolution rate, stability, absorption, etc. Therefore, even for a given compound, the potency may vary with its crystal form. Thus, it is desirable to provide a compound having stable physical properties.

17-cyclopropylmethyl-3,14β-dihydroxy-4,5α-epoxy-6β-[N-methyl-trans-3-(3-furyl)acrylamido]morphinan hydrochloride has been confirmed as an effective active ingredient of analgesic, diuretic and antipruritic agents. U.S. Pat. No. 7,803,942 B2 discloses that the morphinan derivatives have A, B, and C crystal forms. However, its preparation processes are cumbersome, lengthy, and yet require the corresponding seed crystals to prepare the above-mentioned crystals. Furthermore, although the conventional crystal of morphinan derivative has a lower pH variation than its amorphous form, the improvement is still unsatisfactory.

Therefore, in order to optimize the physical properties of the morphinan derivative as well as to simplify the preparation processes of its crystals, it is needed to provide a novel crystal of morphinan derivative and a manufacturing method thereof.

SUMMARY OF THE INVENTION

An object of the present invention is to provide a novel crystal of morphinan derivative, which can be prepared using a hydrogen chloride organic solution, to optimize the physical properties of the morphinan derivative as well as to simplify the preparation processes.

To achieve the above object, the present invention provides an X-form crystal of 17-cyclopropylmethyl-3,14β-dihydroxy-4,5α-epoxy-6β-[N-methyl-trans-3-(3-furyl)acrylamido]morphinan hydrochloride having characteristic diffraction peaks at positions of 2θ of 13.6°(±0.2°), 17.2°(±0.2°), 19.1°(±0.2°), 23.2°(±0.2°), and 23.8°(±0.2°) in a powder X-ray diffraction pattern thereof.

In the X-form crystal of 17-cyclopropylmethyl-3,14β-dihydroxy-4,5α-epoxy-6β-[N-methyl-trans-3-(3-furyl)acrylamido]morphinan hydrochloride according to the present invention, characteristic diffraction peaks are not present at positions of 2θ of 7.2°(±0.2°), 7.6°(±0.2°), 18.5°(±0.2°), and 18.9°(±0.2°) in the powder X-ray diffraction pattern thereof.

Therefore, unlike the conventional crystal, the X-form crystal of 17-cyclopropylmethyl-3,14β-dihydroxy-4,5α-epoxy-6β-[N-methyl-trans-3-(3-furyl)acrylamido]morphinan hydrochloride provided by the present invention has characteristic diffraction peaks at position of 2θ of 13.6°(±0.2°), but not at positions of 2θ of 7.2°(±0.2°), 7.6°(±0.2°), 18.5°(±0.2°), and 18.9°(±0.2°). Thus, the X-form crystal is a novel crystal form of morphinan derivative.

Another object of the present invention is to provide a method for manufacturing a novel crystal of morphinan derivative by using a hydrogen chloride organic solution, without requiring a cumbersome, lengthy preparation process and a seed crystal, thereby simplifying the preparation process of the crystal of morphinan derivative.

To achieve the above object, the present invention provides a method for manufacturing an X-form crystal of 17-cyclopropylmethyl-3,14β-dihydroxy-4,5α-epoxy-6β-[N-methyl-trans-3-(3-furyl)acrylamido]morphinan hydrochloride, comprising: (A) providing a first solution, containing an organic solvent and 17-cyclopropylmethyl-3,14β-dihydroxy-4,5α-epoxy-6β-[N-methyl-trans-3-(3-furyl)acrylamido]morphinan dispersed in the organic solvent; (B) adding a hydrogen chloride organic solution into the first solution to obtain a second solution; and (C) concentrating and drying the second solution to obtain a solid having a X-form crystal of 17-cyclopropylmethyl-3,14β-dihydroxy-4,5α-epoxy-6β-[N-methyl-trans-3-(3-furyl)acrylamido]morphinan hydrochloride, wherein, in a powder X-ray diffraction pattern of the X-form crystal, characteristic diffraction peaks present at positions of 2θ of 13.6°(±0.2°), 17.2°(±0.2°), 19.1°(±0.2°), 23.2°(±0.2°), and 23.8°(±0.2°).

Compared to the conventional method for manufacturing the crystal of morphinan derivative, the above method for manufacturing the X-form crystal of the present invention does not require the addition of seed crystals, and a long time standing agitation or standing, and the whole process takes only about one hour. Therefore, the method for manufacturing the X-form crystal of the present invention can effectively shorten the production time and simplify the preparation process.

In the method for manufacturing the X-form crystal of the present invention, the type of the organic solvent in the step (A) is not particularly limited, as long as it can effectively disperse, suspend, or dissolve the 17-cyclopropylmethyl-3,14β-dihydroxy-4,5α-epoxy-6β-[N-methyl-trans-3-(3-furyl)acrylamido]morphinan, to form a first solution. For example, in an aspect of the present invention, the organic solvent may be a $C_1$-$C_5$ alcohol solvent. Preferably, in an embodiment of the present invention, the organic solvent may be a methanol. Furthermore, the content of the 17-cyclopropylmethyl-3,14β-dihydroxy-4,5α-epoxy-6β-[N-methyl-trans-3-(3-furyl)acrylamido]morphinan in the step (A) is not particularly limited, as long as it can form the first solution. For example, in an aspect of the present invention, the 17-cyclopropylmethyl-3,14β-dihydroxy-4,5α-epoxy-6β-[N-methyl-trans-3-(3-furyl)acrylamido]morphinan in the organic solvent may be present in an amount of 0.001 g/ml to 0.1 g/ml, preferably 0.01 g/ml to 0.05 g/ml, and more preferably 0.02 g/ml to 0.04 g/ml, but the present invention is not limited thereto.

In the method for manufacturing the X-form crystal of the present invention, the type of the hydrogen chloride organic solution in the step (B) is not particularly limited, as long as it may appropriately react with the first solution in the step (A) to form a second solution, but a hydrogen chloride organic solution may be preferably used to optimize the process. Furthermore, the type of the hydrogen chloride organic solution according to the present invention is not particularly limited. For example, the hydrogen chloride organic solution may be a $C_2$-$C_{10}$ ether solution containing hydrogen chloride, a $C_1$-$C_5$ alcohol solution containing hydrogen chloride, a $C_2$-$C_{10}$ ester solution containing hydrogen chloride, or combinations thereof. Preferably, in an aspect of the present invention, the hydrogen chloride organic solution may be a hydrogen chloride ether solution, hydrogen chloride cyclopentyl methyl ether solution, hydrogen chloride isopropanol solution, hydrogen chloride ethyl acetate solution, or combinations thereof, but the present invention is not limited thereto. In addition, in the step (B), the hydrogen chloride concentration of the hydrogen chloride organic solution according to the present invention is not particularly limited, as long as 17-cyclopropylmethyl-3,14β-dihydroxy-4,5α-epoxy-6β-[N-methyl-trans-3-(3-furyl)acrylamido]morphinan hydrochloride can be formed. For example, in an aspect of the present invention, the hydrogen chloride concentration of the hydrogen chloride organic solution may be 0.1N to 10N. Preferably, in another aspect of the present invention, the hydrogen chloride concentration of the hydrogen chloride organic solution may be 0.1N to 6N. More preferably, in further aspect of the present invention, the hydrogen chloride concentration of the hydrogen chloride organic solution may be 0.5N to 6N, but the present invention is not limited thereto.

Further, in the method for manufacturing the X-form crystal of the present invention, the types of the organic solvent used for the first solution and the organic solvent used for the hydrogen chloride organic solution are not particularly limited, as long as the formed 17-cyclopropylmethyl-3,14β-dihydroxy-4,5α-epoxy-6β-[N-methyl-trans-3-(3-furyl)acrylamido]morphinan hydrochloride can be dissolved in the second solution. When the formed 17-cyclopropylmethyl-3,14β-dihydroxy-4,5α-epoxy-6β-[N-methyl-trans-3-(3-furyl) acrylamido]morphinan hydrochloride fails to be dissolved in the second solution, the X-form crystal of 17-cyclopropylmethyl-3,14β-dihydroxy-4,5α-epoxy-6β-[N-methyl-trans-3-(3-furyl)acrylamido]morphinan hydrochloride may not be prepared through concentrating and drying processes. Moreover, when choosing the organic solvent, the organic solvents miscible with each other are preferably selected in order to avoid difficulty in the formation of the 17-cyclopropylmethyl-3,14β-dihydroxy-4,5α-epoxy-6β-[N-methyl-trans-3-(3-furyl)acrylamido]morphinan hydrochloride due to poor miscibility.

In addition, in the method for manufacturing the X-form crystal of the present invention, the ratio between the 17-cyclopropylmethyl-3,14β-dihydroxy-4,5α-epoxy-6β-[N-methyl-trans-3-(3-furyl)acrylamido]morphinan and the hydrogen chloride is not particularly limited, as long as the X-form crystal of 17-cyclopropylmethyl-3,14β-dihydroxy-4,5α-epoxy-6β-[N-methyl-trans-3-(3-furyl)acrylamido]morphinan hydrochloride may be formed. For example, in an aspect of the present invention, in the step (A) and the step (B), a molar ratio of the 17-cyclopropylmethyl-3,14β-dihydroxy-4,5α-epoxy-6β-[N-methyl-trans-3-(3-furyl)acrylamido]morphinan to the hydrogen chloride may be 0.9 to 1.2, but the present invention is not limited thereto.

Further, in the method for manufacturing the X-form crystal of the present invention, any conventional manufacturing method may be used, as long as the desired 17-cyclopropylmethyl-3,14β-dihydroxy-4,5α-epoxy-6β-[N-methyl-trans-3-(3-furyl)acrylamido]morphinan may be formed, and the method for manufacturing morphinan derivative of the present invention is not particularly limited. For example, the method for manufacturing 17-cyclopropylmethyl-3,14β-dihydroxy-4,5α-epoxy-6β-[N-methyl-trans-3-(3-furyl)acrylamido]morphinan disclosed in U.S. Pat. No. 6,323,212 B1 may be used, but the present invention is not limited thereto.

Therefore, according to the method for manufacturing the X-form crystal of the present invention, a novel crystal of 17-cyclopropylmethyl-3,14β-dihydroxy-4,5α-epoxy-6β-[N-methyl-trans-3-(3-furyl)acrylamido]morphinan hydrochloride may be prepared by a quick and easy manufacturing process.

Another object of the present invention is to provide a pharmaceutical composition, which comprises the above novel crystal of the morphinan derivative. The novel crystal has more stable physical and chemical properties, and therefore a stable pharmaceutical composition can be obtained therefrom by optimization of physical properties.

To achieve above object, the present invention provides a pharmaceutical composition, comprising: an effective amount of an X-form crystal of 17-cyclopropylmethyl-3,14β-dihydroxy-4,5α-epoxy-6β-[N-methyl-trans-3-(3-furyl)acrylamido]morphinan hydrochloride; and a pharmaceutically acceptable carrier, wherein, in a powder X-ray diffraction pattern of the X-form crystal, characteristic diffraction peaks are present at positions of 2θ of 13.6°(±0.2°), 17.2°(0.2°), 19.1°(±0.2°), 23.2°(±0.2°), and 23.8°(±0.2°).

In the above-described pharmaceutical composition of the present invention, the dosage of the X-form crystal of 17-cyclopropylmethyl-3,14β-dihydroxy-4,5α-epoxy-6β-[N-methyl-trans-3-(3-furyl)acrylamido]morphinan hydrochloride may be regulated by a person of ordinary skill in the art according to the intended purpose, desired effect, etc., as long as the pharmaceutical composition can achieve the required effect, and the present invention is not particularly limited thereto.

In the above-described pharmaceutical composition of the present invention, a variety of pharmaceutically acceptable carriers may be used, for example, water, ethanol, propylene glycol, polyethylene glycol, Polysorbate 80, glycerin, soybean oil, lactose, white soft sugar, sucrose, sorbitol, microcrystalline cellulose, corn starch, gelatin, dextran, and so on, but the present invention is not particularly limited thereto. Preferably, in an aspect of the present invention, the pharmaceutically acceptable carriers may be water, polyethylene glycol, or combinations thereof.

In the above-described pharmaceutical composition of the present invention, the pharmaceutical composition may further include an anti-oxidant, a synergist, a surfactant, a binder, a thickening agent, an isotonizing agent, a solubilizer, a buffer, a preservative, a base, or combinations thereof. For example, preferable examples of the antioxidant include a water-soluble antioxidant, such as sulfite, nitrite, vitamin C, a thiol derivative, hydroxyquinoline sulfate, etc.; and a fat-soluble antioxidant, such as phenolic compounds, a fat soluble vitamin, an ascorbic acid ester, nordihydroguaiaretic acid, mercaptobenzimidazole, and so on. The preferable example of the synergist may include ethylenediaminetetraacetic acid (EDTA) and its salts, citric acid and its salts, lecithin and so on. Preferable examples of the surfactant include polyoxyethylene hydrogenated castor oil, dehydrated sorbitan sesquioleate, dehydrated sorbitan laurate, dehydrated sorbitan palmitate, glyceryl oleate, gylceryl myristate, polyoxyethylene lauryl ether, polyoxyethylene nonylphenyl ether, and so on. Preferable examples of the binder include hydroxypropylcellulose, hydroxypropylmethylcellulose, polyvinyl pyrrolidone, methyl cellulose and so on. Preferable examples of the thickening agent include gum Arabic, sodium hyaluronate, xanthan gum and so on. Preferable examples of the isotonizing agent include sodium chloride, D-mannitol, xylitol, glucose, etc. Preferable examples of the solubilizer include cyclodextrin and so on. Preferable examples of the buffer include tartaric acid, citric acid, maleic acid, phosphoric acid, succinic acid, lactic acid, acetic acid, sodium hydrogencarbonate, boric acid, sodium borate, magnesium oxide, magnesium hydroxide, and so on. Preferable examples of the preservative include methyl paraoxybenzoate, ethyl paraoxybenzoate, propyl paraoxybenzoate, butyl paraoxybenzoate, benzalkonium chloride and so on. Preferable examples of the base include white petrolatum, Witepsol, Plastibase, liquid paraffin and so on.

Furthermore, the term "effective amount" used in the present invention refers to a dose of each active ingredient required to achieve the desired therapeutic effect for the subject in need. The effective dose may be varied based on the administration route, the carrier, and other ingredients used.

In the above-described pharmaceutical composition of the present invention, the pharmaceutical composition may be administrated by oral, parenteral administration, inhalation spray, topical administration, rectal administration, nasal administration, sublingual administration, vaginal administration, or through the implanted reservoir, etc. The term "parenteral" refers to subcutaneous injection, intradermal injection, intravenous injection, intramuscular injection, intra-articular injection, intraarterial injection, intra-synovial fluid injection, intrathoracic injection, spinal injection, injection at disease site, and intracranial injection or implantation.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENT

Hereinafter, embodiments of the present invention will be explained in detail with reference to the accompanying drawings.

Preparation Example

As shown in the reaction scheme, the desired 17-cyclopropylmethyl-3,14β-dihydroxy-4,5α-epoxy-6β-[N-methyl-trans-3-(3-furyl)acrylamido]morphinan was prepared with reference to the disclosure in U.S. Pat. No. 6,323,212B1.

First, as shown in the step 1, an intermediate A was prepared in advance. In detail, 2.0 g of naltrexone, 1.07 g of N-methylbenzylamine, 10 mg of p-toluene sulfonic acid monohydrate, 50 mL of toluene, and 1 g of benzoic acid were added into a reaction flask and heated under reflux for 12 hours by Dean Stark. Then, until 30 mL of toluene in the reaction flask was distilled off, the heating was stopped and then the reaction solution was cooled down to room temperature. 30 mL of methanol, and 0.4 g of sodium cyanoborohydride were sequentially added to the reaction flask and stirred for 6 hours. The above reaction solution was concentrated and then extracted with 100 mL of dichloromethane and 100 mL of a saturated aqueous sodium bicarbonate solution. The resulting aqueous layer was extracted with 50 mL of methylene chloride twice. Finally, the organic layers were combined, dried by sodium sulfate, filtered and concentrated, to obtain a concentrate of the intermediate A.

Next, as shown in the step 2, an intermediate B was prepared from the intermediate A. In detail, the resulting concentrate of the intermediate A, 50 mL of acetic acid, and 20 mg of 5% Pd/C (50% wet) were added into a pressurized reactor, and stirred under 3 bar of hydrogen at room temperature. After the reaction solution was filtered by diatomaceous earth, the obtained filtrate was neutralized to pH 9.3 with ammonia. Then, the above filtrate was extracted with 100 mL of dichloromethane twice. After this, the organic layers were combined, dried by sodium sulfate, filtered and concentrated, to obtain a concentrate of the intermediate B.

Finally, as shown in the step 3, a desired product was prepared from the intermediate B. In detail, 0.45 g of 3-(3-furyl)acrylic acid, 5 mL of dichloromethane, 0.6 g of oxalyl chloride, and 15 mg of N,N-dimethyl formamide were sequentially added into a 50-ml reaction flask, stirred under nitrogen for 2 hours, and concentrated. Then, the obtained concentrate, the concentrate of the intermediate B, 20 mL of tetrahydrofuran, and 10 mL of pure water, were mixed and stirred at room temperature for 30 minutes. Next, 1 mL of 3N sodium hydroxide solution and 5 mL of methanol were added into the reaction flask, and stirred continuously for 1 hour. The filtrate of the resulting reaction solution was extracted with 100 mL of dichloromethane twice, and the organic layers were combined, dried by sodium sulfate, filtered and concentrated. Finally, the concentrate was purified by column chromatography with 1.5% methanol/dichloromethane solution, to obtain 0.6 g of the desired product, 17-cyclopropylmethyl-3,14β-dihydroxy-4,5α-epoxy-6β-[N-methyl-trans-3-(3-furyl)acrylamido]morphinan.

[Reaction Scheme]

intermediate A

Step 2 intermediate B

Thus, a sufficient amount of 17-cyclopropylmethyl-3,14β-dihydroxy-4,5α-epoxy-6β-[N-methyl-trans-3-(3-furyl)acrylamido]morphinan was prepared by the above described method for use in the following Examples.

EXAMPLES 1 TO 6

First, 17-cyclopropylmethyl-3,14β-dihydroxy-4,5α-epoxy-6β-[N-methyl-trans-3-(3-furyl)acrylamido]morphinan was dispersed in methanol solvent, and an hydrogen chloride organic solution was added thereto to form a second solution. Then, after stirring for 15 minutes, the second solution was concentrated and dried to obtain a crystal of 17-cyclopropylmethyl-3,14β-dihydroxy-4,5α-epoxy-6β-[N-methyl-trans-3-(3-furyl)acrylamido]morphinan hydrochloride. The amount of each component in Examples 1-6 is shown in Table 1.

TABLE 1

| | | | hydrogen chloride organic solution | |
|---|---|---|---|---|
| | morphinan derivative * (g) | Methanol (ml) | Amount (ml) | HCl concentration | type |
| Example 1 | 9.6 | 288 | 20 | 1N | ethyl ether |
| Example 2 | 13.1 | 350 | 27.3 | | ether |
| Example 3 | 31.4 | 1011 | 65.4 | | |
| Example 4 | 1.2 | 36 | 0.88 | 1N | Cyclopentyl methyl ether |
| Example 5 | 16.5 | 525 | 6.8 | 5.3N | Isopropanol |
| Example 6 | 1.2 | 36 | 2.6 | 1N | Ethyl acetate |

Figure 1A:
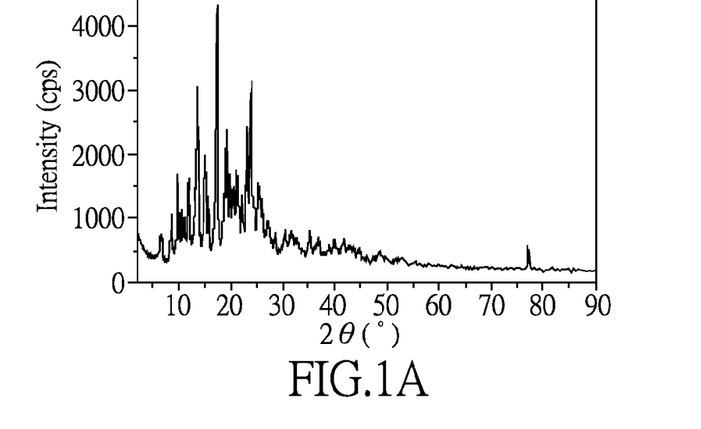
FIGS. 1A-1C show the powder X-ray diffraction patterns of Examples 1-3 according to the present invention.
Figure 1B:
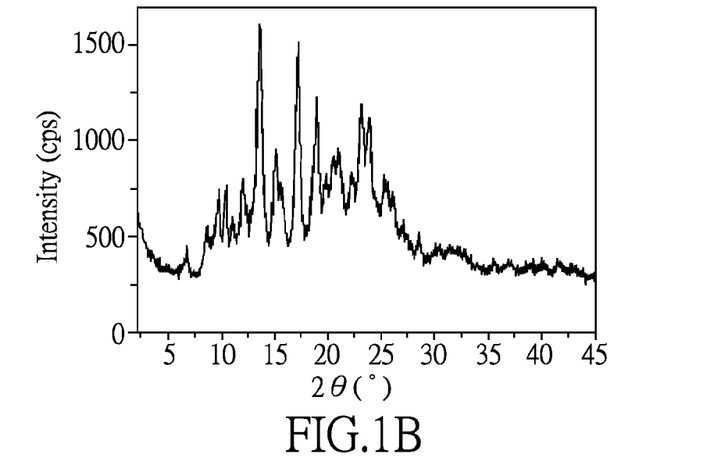
Figure 1C:
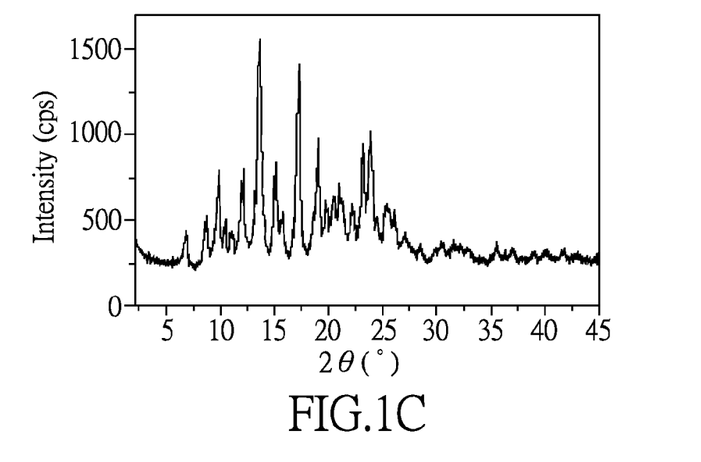
Figure 2:
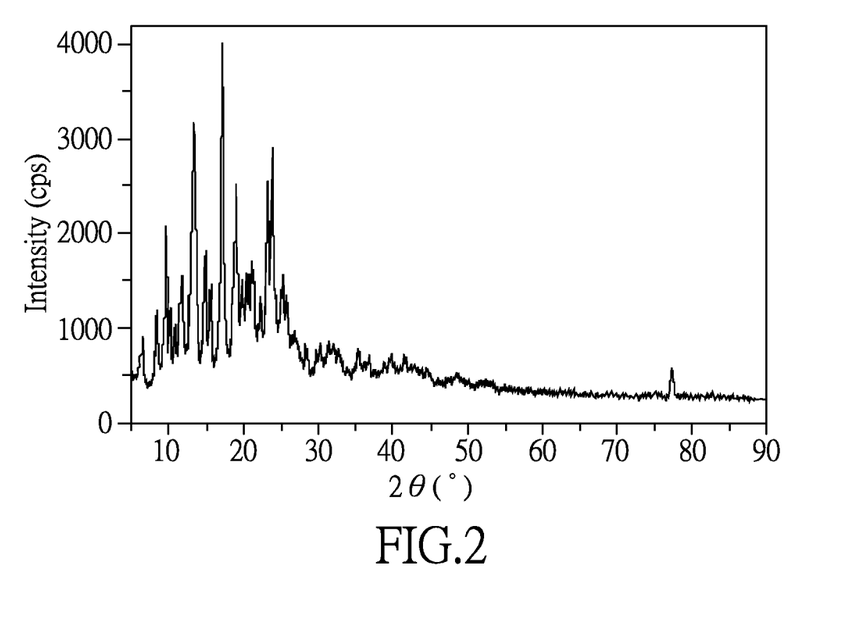
FIG. 2 shows the powder X-ray diffraction patterns of Example 4 according to the present invention.
Figure 3:
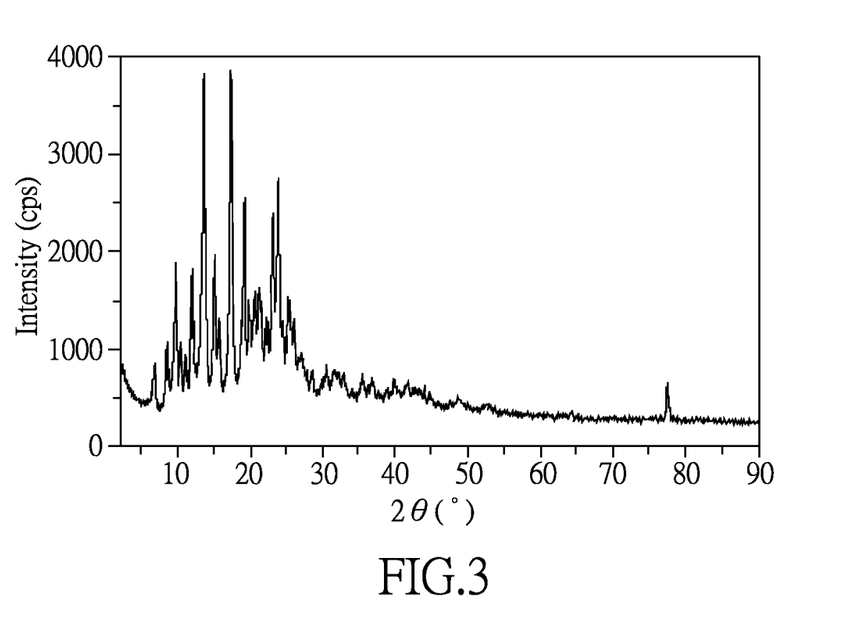
FIG. 3 shows the powder X-ray diffraction patterns of Example 5 according to the present invention.
Figure 4:
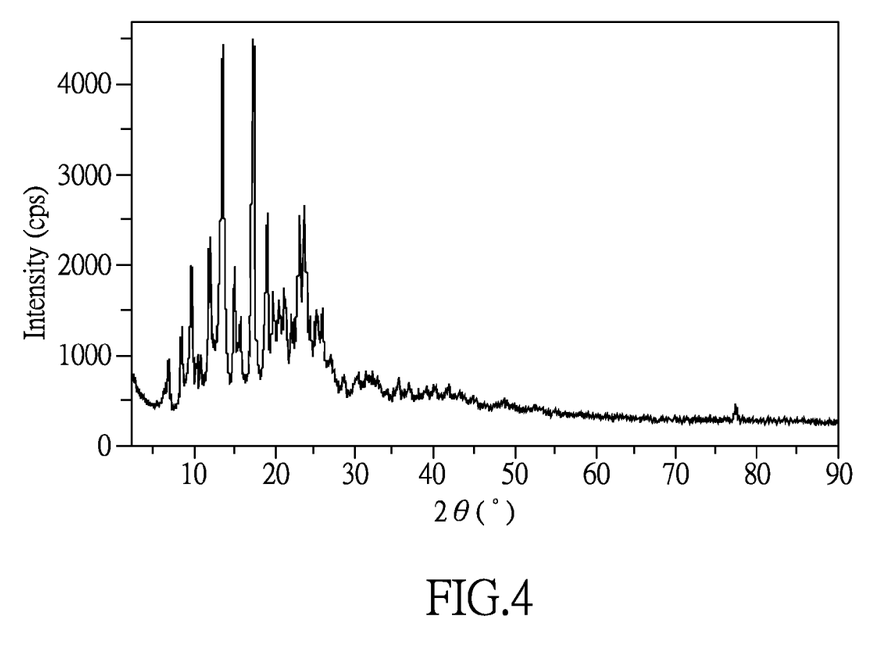
FIG. 4 shows the powder X-ray diffraction patterns of Example 6 according to the present invention.

* morphinan derivative:
17-cyclopropylmethyl-3,14β-dihydroxy-4,5α-epoxy-6β-[N-methyl-trans-3-(3-furyl)acrylamido]morphonan Please refer to FIGS. 1A-1C, which show the powder X-ray diffraction patterns of 17-cyclopropylmethyl-3,14β-dihydroxy-4,5α-epoxy-6β-[N-methyl-trans-3-(3-furyl)acrylamido]morphinan hydrochloride obtained from Examples 1-3 respectively. Please refer to FIGS. 2-4, which show the powder X-ray diffraction patterns of 17-cyclopropylmethyl-3,14β-dihydroxy-4,5α-epoxy-6β-[N-methyl-trans-3-(3-furyl)acrylamido]morphinan hydrochloride obtained from Examples 4-6 respectively. In the powder X-ray diffraction patterns of 17-cyclopropylmethyl-3,14β-dihydroxy-4,5α-epoxy-6β-[N-methyl-trans-3-(3-furyl)acrylamido]morphinan hydrochloride obtained from Examples 1-6, the main characteristic diffraction peaks of each example are shown in Table 2.

TABLE 2

| | 2θ | | | | |
|---|---|---|---|---|---|
| Example 1 | 13.5 | 17.2 | 19.1 | 23.2 | 23.9 |
| Example 2 | 13.6 | 17.2 | 19.0 | 23.1 | 23.8 |

TABLE 2-continued

| | 2θ | | | | |
|---|---|---|---|---|---|
| Example 3 | 13.6 | 17.3 | 19.1 | 23.2 | 23.9 |
| Example 4 | 13.6 | 17.2 | 19.1 | 23.1 | 23.8 |
| Example 5 | 13.6 | 17.2 | 19.1 | 23.1 | 23.8 |
| Example 6 | 13.6 | 17.2 | 19.1 | 23.1 | 23.8 |

As shown in Table 2, unlike the conventional crystal, the crystal forms obtained from Examples 1-6 had characteristic diffraction peaks at a position of 2θ of 13.6°(±0.2°), but not at positions of 2θ of 7.2°(±0.2°), 7.6°(±0.2°), 18.5°(±0.2°), and 18.9°(±0.2°). Accordingly, the 17-cyclopropylmethyl-3,14β-dihydroxy-4,5α-epoxy-6β-[N-methyl-trans-3-(3-furyl)acrylamido]morphinan hydrochloride of the present invention has a novel crystal form, an X-form crystal.

COMPARATIVE EXAMPLE 1

Figure 5A:
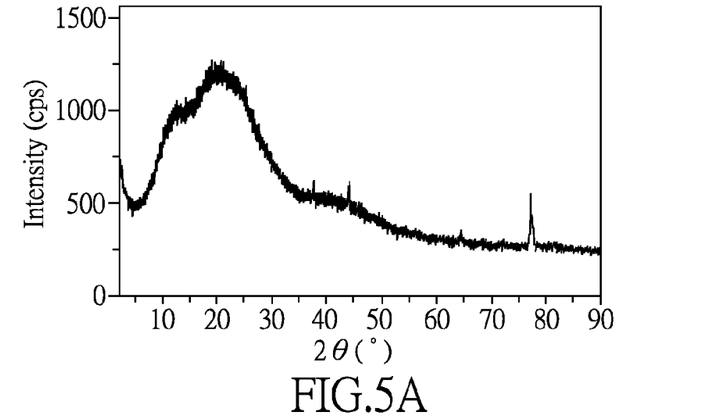
FIGS. 5A-5C show the powder X-ray diffraction patterns of Comparative Examples 1-3 according to the present invention.

First, 14.3 g of 17-cyclopropylmethyl-3,14β-dihydroxy-4,5α-epoxy-6β-[N-methyl-trans-3-(3-furyl)acrylamido]morphinan was dispersed in 500 ml of methylene chloride solvent, and 30 ml of 1N hydrogen chloride diethyl ether solution was added thereto to form a mixed solution. Then, after stirring for 15 minutes, a precipitate was formed in the mixed solution. The precipitate was filtered to obtain a solid which was dried under vacuum to obtain 11 g of a white solid. The resulting white solid was analyzed by an X-ray diffractometer, and the result is shown in FIG. 5A.

COMPARATIVE EXAMPLE 2

Comparative Example 2 is substantially similar to Comparative Example 1, except that different amounts of the components were used. First, 1.2 g of 17-cyclopropylmethyl-3,14β-d hydroxy-4,5α-epoxy-6β-[N-methyl-trans-3-(3-furyl)acrylamido]morphinan was dispersed in 125 ml of methylene chloride solvent, and 1.6 ml of 1N hydrogen chloride diethyl ether solution was added thereto to form a mixed solution. Then, a precipitate was formed in the mixed solution. The precipitate was filtered to obtain a solid which was dried under vacuum to obtain 0.9 g of a white solid. The resulting white solid was analyzed by an X-ray diffractometer, and the result is shown in FIG. 5B.

COMPARATIVE EXAMPLE 3

First, 1.2 g of 17-cyclopropylmethyl-3,14β-dihydroxy-4,5α-epoxy-6β-[N-methyl-trans-3-(3-furyl)acrylamido]morphinan was dispersed in 36 ml of ethanol solvent, and 2.6 ml of 1N hydrochloric acid solution was added thereto to form a mixed solution. Then, after stirring for 15 minutes, the mixed solution was concentrated and dried to obtain a white solid. The resulting white solid was analyzed by an X-ray diffractometer, and the result is shown in FIG. 5C.

Figure 5B:
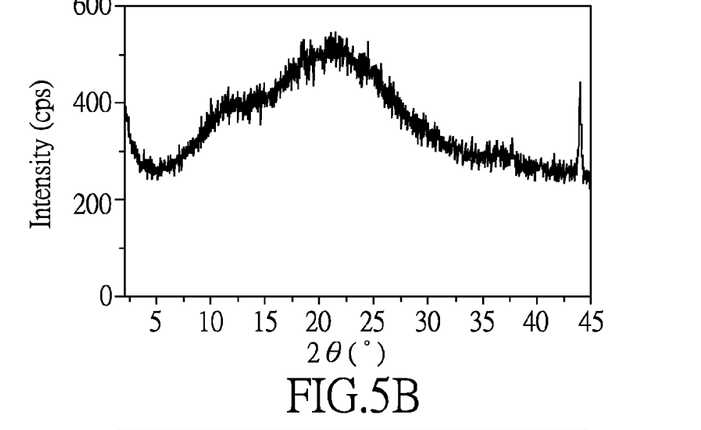
Figure 5C:
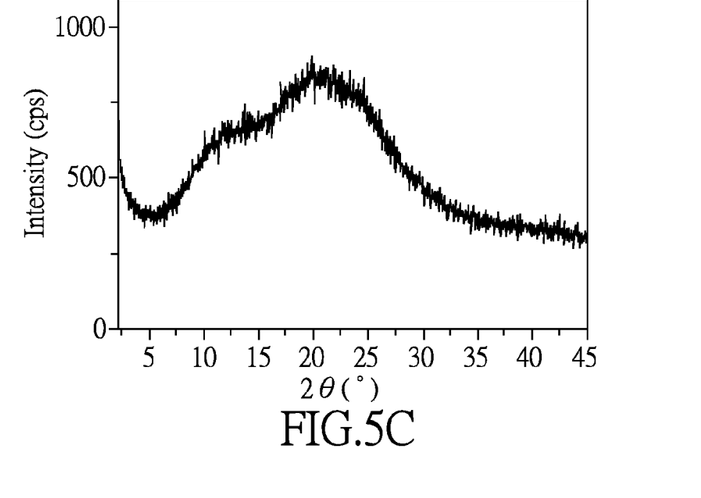

As shown in FIGS. 5A-5C, the products prepared in Comparative Examples 1-3 did not possess the characteristic diffraction peaks of crystal. That is, 17-cyclopropylmethyl-3,14β-dihydroxy-4,5α-epoxy-6β-[N-methyl-trans-3-(3-furyl)acrylamido]morphinan hydrochloride formed by Comparative Examples 1-3 was not crystalline, but amorphous 17-cyclopropylmethyl-3,14β-dihydroxy-4,5α-epoxy-6β-[N-methyl-trans-3-(3-furyl)acrylamido]morphinan hydrochloride.

COMPARATIVE EXAMPLES 4 to 6

In Comparative Examples 4-6, amorphous 17-cyclopropylmethyl-3,14β-dihydroxy-4,5α-epoxy-6β-[N-methyl-trans-3-(3-furyl)acrylamido]morphinan hydrochloride was prepared following the method described in Reference Examples 1-3 of U.S. Pat. No. 7,803,942B2.

COMPARATIVE EXAMPLE 7 to 9

In Comparative Examples 7-9, the A-form crystal of 17-cyclopropylmethyl-3,14β-dihydroxy-4,5α-epoxy-6β-[N-methyl-trans-3-(3-furyl)acrylamido]morphinan hydrochloride was prepared following the method described in Examples 1-3 of U.S. Pat. No. 7,803,942B2.

pH Stability Test

First, 100 mg of the X-form crystal solid of Examples 1 to 3, and the amorphous solid of Comparative Examples 1-6 were dissolved in 10 ml of deionized water respectively. Then, pH value of the resulting solutions was measured with a pH meter (Type No: Mettler Toledo MP 250). The measurement results are shown in Table 3, wherein the result of the amorphous and A-form crystals of Comparative Examples 4-9 was quoted from U.S. Pat. No. 7,803,942B2.

TABLE 3

| Crystal | | pH | ΔpH |
|---|---|---|---|
| X-form | Example 1 | 3.5 | 0.1 |
| | Example 2 | 3.6 | |
| | Example 3 | 3.6 | |
| amorphous | Comparative Example 1 | 4.4 | 1.8 |
| | Comparative Example 2 | 2.6 | |
| | Comparative Example 3 | 3.7 | |
| | Comparative Example 4 | 3.7 | |
| | Comparative Example 5 | 4.7 | 1.2 |
| | Comparative Example 6 | 3.5 | |
| A-form | Comparative Example 7 | 5.8 | 0.4 |
| | Comparative Example 8 | 5.4 | |
| | Comparative Example 9 | 5.6 | |

As shown in Table 3, ΔpH of the amorphous 17-cyclopropylmethyl-3,14β-dihydroxy-4,5α-epoxy-6β-[N-methyl-trans-3-(3-furyl)acrylamido]morphinan hydrochloride prepared in Comparative Examples 1-3 and the amorphous 17-cyclopropylmethyl-3,14β-dihydroxy-4,5α-epoxy-6β-[N-methyl-trans-3-(3-furyl)acrylamido]morphinan hydrochloride disclosed by U.S. Pat. No. 7,803,942B2 (Comparative Examples 4-6) were much larger than the X-form crystal of 17-cyclopropylmethyl-3,14β-dihydroxy-4,5α-epoxy-6β-[N-methyl-trans-3-(3-furyl)acrylamido]morphinan hydrochloride prepared by Examples 1-3 of the present invention. In addition, compared to the results of the A-form crystal of 17-cyclopropylmethyl-3,14β-dihydroxy-4,5α-epoxy-6β-[N-methyl-trans-3-(3-furyl)acrylamido]morphinan hydrochloride disclosed by U.S. Pat. No. 7,803,942B2 (Comparative Examples 7-9), the X-form crystal of 17-cyclopropylmethyl-3,14β-dihydroxy-4,5α-epoxy-6,3-[N-methyl-trans-3-(3-furyl)acrylamido]morphinan hydrochloride prepared by Examples 1-3 of the present invention also had a lower ΔpH, indicating a more stable and consistent pH value.

Light Stability Test

First, 1 mg of the X-form crystal solid of Examples 1 to 3, and the amorphous solid of Comparative Examples 1-3 were sealed in a 1 mL glass sample bottle respectively. Then, the above sample was illuminated for five days at 25, 4700 LUX, under 30% humidity. Finally, the purity of the samples of above Examples and Comparative Examples was analyzed by high performance liquid chromatography separately. The results are shown in Table 4.

TABLE 4

| Crystal | | Illumination (purity %) | | Difference in purity before and after illumination (%) | Range of difference between the maximum and minimum of purity |
|---|---|---|---|---|---|
| | | Day 0 | Day 5 | | |
| X-form | Example 1 | 99.78 | 99.56 | 0.26 | 0.26-0.73 |
| | Example 2 | 99.92 | 99.19 | 0.73 | |
| | Example 3 | 100.00 | 99.72 | 0.28 | |
| amorphous | Comparative Example 1 | 92.78 | 90.99 | 1.79 | 1.65-4.21 |
| | Comparative Example 2 | 99.73 | 95.52 | 4.21 | |
| | Comparative Example 3 | 99.84 | 98.19 | 1.65 | |

Accordingly, the results from the pH stability and light stability test show that the X-form crystal of 17-cyclopropylmethyl-3,14β-dihydroxy-4,5α-epoxy-6β-[N-methyl-trans-3-(3-furyl)acrylamido]morphinan hydrochloride prepared by the present invention had excellent stability, and the process of the present invention was simplified and less time consuming as compared to prior art processes. Therefore, the X-form crystal of 17-cyclopropylmethyl-3,14β-dihydroxy-4,5α-epoxy-6β-[N-methyl-trans-3-(3-furyl)acrylamido]morphinan hydrochloride of the present invention and the manufacturing method thereof can provide improved physical properties, and also simplify the manufacturing process.

Preparation Example of Pharmaceutical Composition

In this Preparation Example, a pharmaceutical composition was prepared for a soft capsule. However, this is only one exemplary preparation method of the pharmaceutical composition, and the present invention is not limited thereto.

First, 40 mg of the X-form crystal solid prepared in the above Examples, and 0.1 g of sodium thiosulfate were dissolved in 2 g of deionized water. Then, polyethylene glycol (trade name: Polyethylene glycol 400) was added so as to have a total weight of 100 g, thus completing the pharmaceutical composition for soft capsules.

It should be understood that these examples are merely illustrative of the present invention and the scope of the invention should not be construed to be defined thereby, and the scope of the present invention will be limited only by the appended claims.

What is claimed is:

1. A X-form crystal of 17-cyclopropylmethyl-3,14β-dihydroxy-4,5α-epoxy-6β-[N-methyl-trans-3-(3-furyl)acrylamido]morphinan hydrochloride, having characteristic diffraction peaks at positions of 2θ of 13.6°(±0.2°), 17.2°(±0.2°), 19.1°(±0.2°), 23.2°(±0.2°), and 23.8°(±0.2°) in a powder X-ray diffraction pattern thereof.

2. A method for manufacturing an X-form crystal of 17-cyclopropylmethyl-3,14β-dihydroxy-4,5α-epoxy-6β-[N-methyl-trans-3-(3-furyl)acrylamido]morphinan hydrochloride, comprising:
   (A) providing a first solution, containing an organic solvent and 17-cyclopropylmethyl-3,14β-dihydroxy-4,5α-epoxy-6β-[N-methyl-trans-3-(3-furyl)acrylamido]morphinan dispersed in the organic solvent;
   (B) adding a hydrogen chloride organic solution into the first solution to obtain a second solution; and
   (C) concentrating and drying the second solution to obtain a solid having an X-form crystal of 17-cyclopropylmethyl-3,14β-dihydroxy-4,5α-epoxy-6β-[N-methyl-trans-3-(3-furyl)acrylamido]morphinan hydrochloride,
   wherein, in a powder X-ray diffraction pattern of the X-form crystal, characteristic diffraction peaks are present at positions of 2θ of 13.6°(±0.2°), 17.2°(±0.2°), 19.1°(±0.2°), 23.2°(±0.2°), and 23.8°(±0.2°).

3. The method for manufacturing of claim 2, wherein, in the step (A), the organic solvent is a $C_1$-$C_5$ alcohol solvent.

4. The method for manufacturing the X-form crystal of claim 2, wherein, in the step (A), the 17-cyclopropylmethyl-3,14β-dihydroxy-4,5α-epoxy-6β-[N-methyl-trans-3-(3-furyl)acrylamido]morphinan in the organic solvent is present in an amount of 0.001 g/ml to 0.1 g/ml.

5. The method for manufacturing the X-form crystal of claim 2, wherein, in the step (B), the hydrogen chloride organic solution is a hydrogen chloride organic solvent.

6. The method for manufacturing the X-form crystal of claim 2, wherein, in the step (B), the hydrogen chloride organic solution is a $C_2$-$C_{10}$ ether solution containing hydrogen chloride, a $C_1$-$C_5$ alcohol solution containing hydrogen chloride, a $C_2$-$C_{10}$ ester solution containing hydrogen chloride, or combinations thereof.

7. The method for manufacturing the X-form crystal of claim 2, wherein, in the step (B), the hydrogen chloride organic solution includes hydrogen chloride in a concentration of 0.1N to 10N.

8. The method for manufacturing the X-form crystal of claim 2, wherein, in the steps (A) and (B), a molar ratio of the 17-cyclopropylmethyl-3,14β-dihydroxy-4,5α-epoxy-6β-[N-methyl-trans-3-(3-furyl)acrylamido]morphinan to the hydrogen chloride is 0.9 to 1.2.

9. A pharmaceutical composition, comprising:
   an effective amount of an X-form crystal of 17-cyclopropylmethyl-3,14β-dihydroxy-4,5α-epoxy-6β-[N-methyl-trans-3-(3-furyl)acrylamido]morphinan hydrochloride; and
   a pharmaceutically acceptable carrier,
   wherein, in a powder X-ray diffraction pattern of the X-form crystal, characteristic diffraction peaks are present at positions of 2θ of 13.6°(±0.2°), 17.2°(±0.2°), 19.1°(±0.2°), 23.2°(±0.2°), and 23.8°(±0.2°).

10. The pharmaceutical composition of claim 9, wherein the pharmaceutically acceptable carrier is water, polyethylene glycol or combinations thereof.

* * * * *